United States Patent
Perszyk

(10) Patent No.: US 10,925,756 B2
(45) Date of Patent: Feb. 23, 2021

(54) COLLAPSIBLE MEDICAL DEVICE HAVING AN OPEN LUMEN

(71) Applicant: St. Jude Medical, Cardiology Division, Inc., St. Paul, MN (US)

(72) Inventor: Brian Perszyk, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 274 days.

(21) Appl. No.: 15/959,402

(22) Filed: Apr. 23, 2018

(65) Prior Publication Data

US 2018/0318548 A1 Nov. 8, 2018

Related U.S. Application Data

(60) Provisional application No. 62/500,737, filed on May 3, 2017.

(51) Int. Cl.
*A61F 2/88* (2006.01)
*A61F 2/90* (2013.01)
(Continued)

(52) U.S. Cl.
CPC ............ *A61F 2/885* (2013.01); *A61F 2/90* (2013.01); *A61F 2/2418* (2013.01);
(Continued)

(58) Field of Classification Search
CPC .......... A61F 2/24–2424; A61F 2/82–90; A61F 2250/0028; A61F 2210/0014; A61F 2250/0096–0098
See application file for complete search history.

(56) References Cited

U.S. PATENT DOCUMENTS

| 2010/0234937 A1* | 9/2010 | Wang | A61B 17/12104 |
| | | | 623/1.18 |
| 2013/0211492 A1* | 8/2013 | Schneider | A61F 2/90 |
| | | | 623/1.11 |

(Continued)

FOREIGN PATENT DOCUMENTS

| CN | 102551933 A | * | 7/2012 | ............... A61F 2/90 |
| WO | 9742878 A1 | | 11/1997 | |
| WO | 0172367 A1 | | 10/2001 | |

OTHER PUBLICATIONS

Machine translation of CN102551933, pp. 1-10, date accessed May 21, 2020. (Year: 2020).*

(Continued)

*Primary Examiner* — Rebecca S Preston
(74) *Attorney, Agent, or Firm* — Armstrong Teasdale LLP

(57) ABSTRACT

The present disclosure provides collapsible medical devices that are formed from a braided tubular member configured to allow the braided tubular member to be terminated into one or more marker bands while maintaining an open lumen from a proximal end to a distal end. The collapsible medical device including the braided tubular member can be easily pulled down into a delivery sheath or other delivery device so that it is suitable for use with a number of delivery devices. The marker bands, which provide one or more attachment points for a medical device/delivery system, are positioned at one or more locations on the braid such that the braid is fixed and cannot unravel, thus preventing entanglement between individual braid wires and malformation of the device.

6 Claims, 13 Drawing Sheets

(51) Int. Cl.
　　　*A61M 25/00*　　　(2006.01)
　　　*A61M 25/01*　　　(2006.01)
　　　*A61F 2/24*　　　　(2006.01)

(52) U.S. Cl.
　　　CPC .............. *A61F 2210/0014* (2013.01); *A61F 2220/0025* (2013.01); *A61F 2240/001* (2013.01); *A61F 2250/0017* (2013.01); *A61F 2250/0096* (2013.01); *A61F 2250/0098* (2013.01); *A61M 25/005* (2013.01); *A61M 25/0023* (2013.01); *A61M 2025/0024* (2013.01); *A61M 2025/0025* (2013.01); *A61M 2025/0177* (2013.01)

(56) References Cited

U.S. PATENT DOCUMENTS

| | | |
|---|---|---|
| 2013/0245745 A1 | 9/2013 | Vong et al. |
| 2014/0249567 A1 | 9/2014 | Adams et al. |
| 2014/0249568 A1 | 9/2014 | Adams et al. |
| 2016/0262880 A1 | 9/2016 | Li et al. |

OTHER PUBLICATIONS

International Search Report and Written Opinion issued in International Patent Application No. PCT/US2018/028808 dated Sep. 6, 2018, 18 pages.

Invitation to Pay Additional Fees issued in International Patent Application No. PCT/US2018/028808 on Jul. 11, 2018, 12 pages.

\* cited by examiner

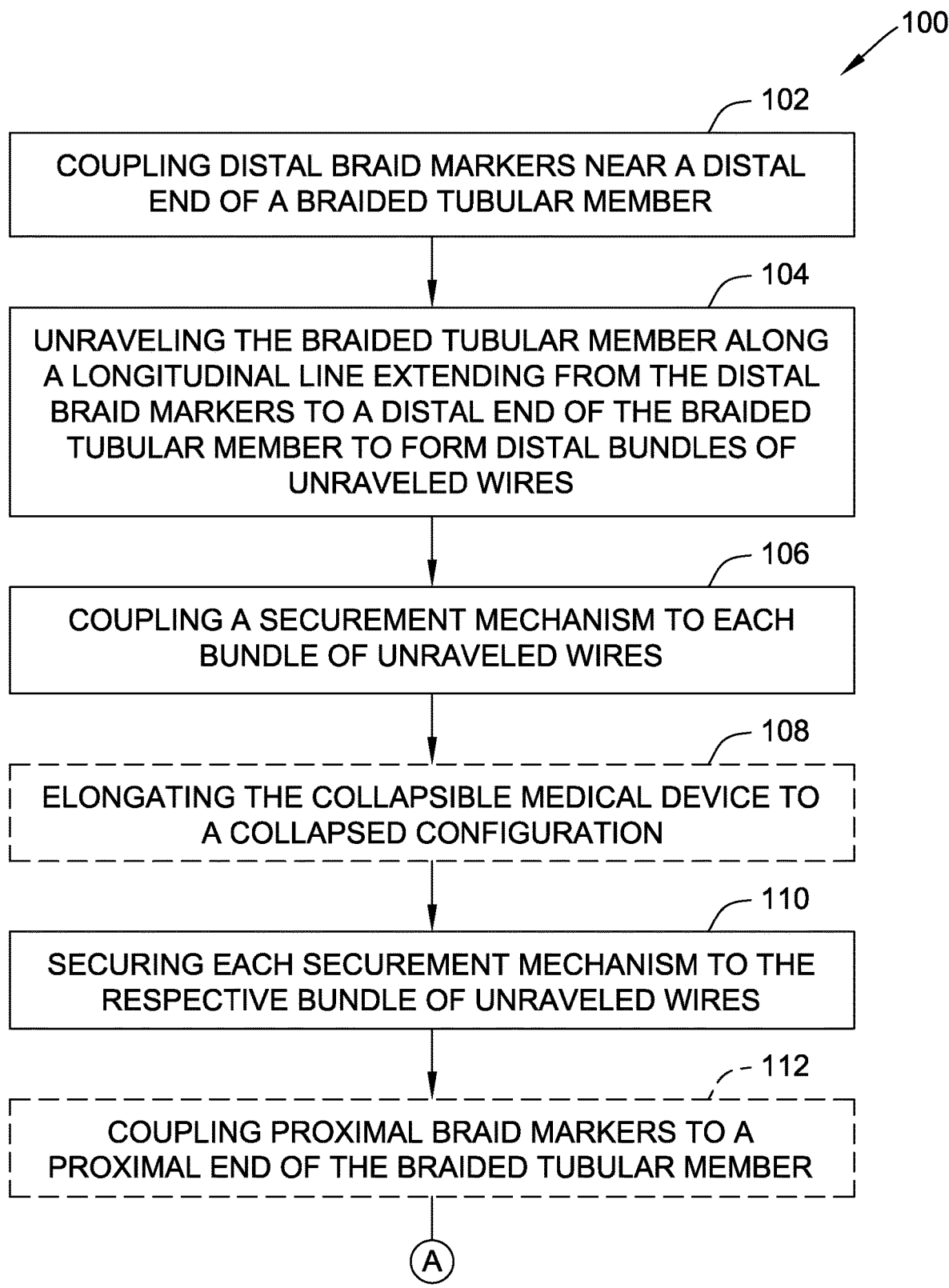

COLLAPSIBLE MEDICAL DEVICE HAVING AN OPEN LUMEN

CROSS REFERENCE OF RELATED APPLICATION

This application claims priority to U.S. Provisional Application Ser. No. 62/500,737, filed May 3, 2017 which is incorporated by reference in its entirety.

BACKGROUND OF THE DISCLOSURE

Field of the Disclosure

The present disclosure generally relates to a collapsible medical device and methods of making and using the same. In particular, the present disclosure relates to a collapsible medical device formed from a braided tubular member that has an open lumen from a proximal end to a distal end. The collapsible medical device may be collapsed into a delivery device for delivery or attached to another medical device. Methods of manufacturing and using the collapsible medical devices including the open lumen are also disclosed.

Background Art

A wide variety of intravascular medical devices are used in various medical procedures within the body. Certain intravascular medical devices, such as catheters and guidewires, are generally used simply to deliver fluids or other medical devices to specific locations within a patient's body, such as a selective site within the vascular system. Other, frequently more complex, collapsible intravascular devices are used in treating specific conditions, such as devices used in removing vascular occlusions, for treating septal defects, for valve replacements, stent introduction, and the like. Many of these more complex collapsible intravascular devices are constructed, at least in part, of a braided tubular member, such as a nitinol braided tubular member.

In many cases where it is desirable to utilize an intravascular cardiac collapsible medical device, it may be advantageous to provide a collapsible medical device formed from a braided tubular member that includes an open lumen from a proximal end to a distal end to allow for the passage of fluids and/or for the introduction of a separate medical device therethrough. Such a collapsible medical device may be particularly advantageous for thoracic grafts, embolic protection devices, and atrial seals for transcatheter mitral valves, for example.

SUMMARY OF THE DISCLOSURE

The present disclosure is directed to a collapsible medical device. The collapsible medical device comprises: (i) a tubular member formed of a plurality of wires and having a preset, expanded configuration and a collapsed configuration, the tubular member having a center portion wherein the wires are in a braided configuration, and a distal end and a proximal end wherein the wires are in an unraveled configuration; (ii) an open lumen extending from the proximal end to the distal end configured to allow passage of a fluid therethrough in the preset, expanded configuration; (iii) at least one securement mechanism coupled to the proximal end; and (iv) at least one securement mechanism coupled to the distal end. Each securement mechanism is configured to secure at least a portion of the plurality of wires in the unraveled configuration near an outer circumference of the open lumen.

The present disclosure is further directed to a collapsible medical device. The collapsible medical device comprises: (i) an inverted braided tubular member comprising a first set of wire ends longitudinally aligned with a second set of wire ends at a distal end thereof, and an open lumen extending between the distal end and a proximal end of the inverted braided tubular member; and (ii) at least one securement mechanism positioned near an outer circumference of the inverted braided tubular member on the distal end thereof.

The present disclosure is further directed to a method of forming a collapsible medical device having an open lumen. The method comprises: (i) coupling at least one braid marker to a tubular member comprising a plurality of braided wires, the tubular member having a distal end and a proximal end; (ii) unraveling the braided member along a longitudinal line extending from the at least one braid marker to the proximal end or the distal end to form one or more sections of unraveled wires; (iii) coupling a securement mechanism to each section of unraveled wires; and (iv) securing each securement mechanism to the respective section of unraveled wires.

The present disclosure is further directed to a method of forming a collapsible medical device having an open lumen. The method comprises: (i) inverting a proximal end of a braided tubular member over itself toward a distal end of the braided tubular member to form an inner layer and an outer layer; (ii) longitudinally aligning wire ends of the proximal end and the distal end of the braided tubular member; (iii) coupling at least one braid marker to the inner and outer layer of the braided tubular member; (iv) unraveling the inner layer and the outer layer along a longitudinal line extending from each braid marker to the wire ends to form a section of unraveled wires between each respective braid marker; (v) coupling a securement mechanism to each section of unraveled wires; and (vi) securing each securement mechanism to the respective section of unraveled wires.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIGS. 6A and 6B are flow diagrams of a method of forming a collapsible medical device including an open lumen;

DETAILED DESCRIPTION OF THE DISCLOSURE

Figure 1:
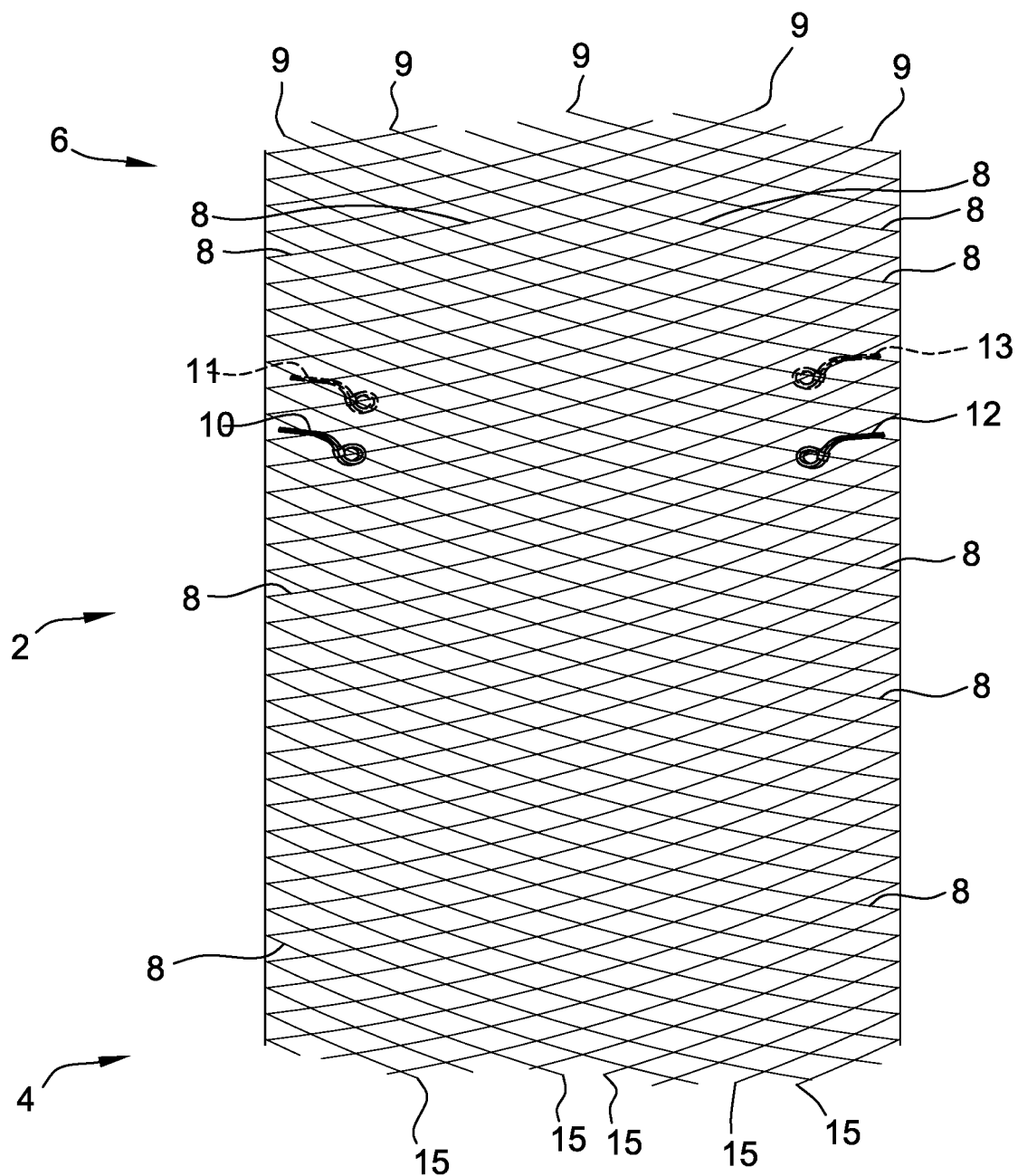
FIG. 1 is a perspective view of a braided tubular member suitable for the forming of a collapsible medical device of the present disclosure.

The fabrication of collapsible medical devices constructed of a braided tubular member that include an open lumen from the distal end to the proximal end has, to date, been difficult. Some of the previous methods used to form a desired open lumen extending from the distal end to the proximal end of the collapsible medical device have included the use of a forming tool that is forced through a pick of the braided material to open up and spread the braid apart. This method, however, has been met with generally ineffective results since the forming tool size has been limited by the amount of braid that could be stretched around the tool. Other methodologies employed have not produced the desired results. As such, it would be desirable to provide a collapsible medical device including an open lumen from a proximal end to a distal end that could easily be collapsed and introduced into a delivery sheath or other delivery device, or easily attached to another medical device.

The present disclosure is directed to a collapsible medical device that includes a braided tubular member, such as a nitinol braided tubular member, where the braided pattern is configured to allow wire ends of the braided tubular member to be terminated into one or more securement/attachment points while maintaining a complete open lumen through the collapsible medical device. Along with providing a termination point, the securement/attachment points may also act as a point for the attachment of another medical device and/or a medical delivery device. After formation, the collapsible medical devices of the present disclosure including the open lumen may be further heat treated to a desired pre-set conformation. In many embodiments, the collapsible medical device including the braided tubular member is constructed such that can be easily pulled down into a delivery sheath or other delivery device so that it is suitable for use with a number of medical and delivery devices.

The securement/attachment points, which, as noted above, may provide one or more attachment points for attachment to another medical device, such as a stent, or attachment to a delivery system, offer additional advantages as well. These securement/attachment points are positioned on the braid such that the braid is fixed and cannot unravel, thus preventing entanglement between individual braid wires and unwanted malformation of the braided device. Additionally, free wire (or strand) ends are eliminated, thus reducing any potential unwanted contact of free wire ends with other materials or tissue in the body. The number of securement/attachment points utilized in the forming of the collapsible medical devices of the present disclosure is a design choice as further discussed herein, as the larger the number of securement/attachment points used the shorter the securement/attachment sections become. In some embodiments described herein, the collapsible medical device includes one or more securement/attachment points at both a distal end and a proximal end of the collapsible medical device. In other embodiments described herein, the braided tubular member is inverted over itself during the forming process such that one or more securement/attachment points are located only at a single end of the collapsible medical device.

The collapsible medical devices of the present disclosure are formed from a braided tubular member that comprises a plurality of wires. In many embodiments, the wires are all of generally the same length; that is, the wires that comprise the braided tubular member are all substantially the same length or exactly the same length. In other embodiments, the wires forming the plurality of wires may be of different lengths. In some embodiments, by having the wires of substantially or exactly the same length throughout the collapsible medical device, the braided tubular member may be easily pulled down into a catheter or other delivery device after formation as described herein. The braided tubular member may be fabricated with any number of wires that terminate into one or more securement/attachment points, as further described herein. In many embodiments described herein, it is not required that an equal number of wires be divided among the securement/attachment points; that is, when more than one securement/attachment point is utilized on the braided tubular member, each securement/attachment point may or may not include the same number of wires, as further described below.

The braided tubular members used to form the collapsible medical devices of the present disclosure are generally constructed of a plurality of wires or strands generally provided as a tubular metal fabric. The tubular metal fabric is formed of woven metal wires or strands that are heat set after formation into the desired configuration as more fully described below. The woven metal wires are a plurality of conventional wires that have a predetermined relative orientation between the wires. The wires define two sets of essentially parallel generally helical stands, with the strands of one set having a "hand", i.e., a direction of rotation, opposite that of the other set. These helical wires define a generally tubular metal fabric, known in the metal fabric industry as a tubular braid.

The pitch of the wires (i.e., the angle defined between the turns of the wire and the axis of the braid) and the pick of the fabric (i.e., the number of wire crossovers per unit length) may be adjusted as known by those of skill in the art based on the disclosure herein to increase/decrease/optimize the rigidity/strength as desired for a particular application. The wires of the metal fabric used to construct the collapsible medical devices described herein are desirably formed of a material that is both resilient and that can be heat treated to substantially set a desired shape. Materials that are suitable for this purpose include a cobalt-based low thermal expansion alloy referred to in the field as Elgeloy, nickel-based high temperature high-strength superalloys commercially available from Haynes International under the trade name Hastelloy, nickel-based heat treatable alloys sold under the name Incoloy by International Nickel, and a number of different grades of stainless steel. An important factor in choosing a suitable material for the wires is that the wires retain a suitable amount of the deformation induced by a molding process when subjected to a predetermined heat treatment.

One class of materials that are desirable is memory-shape alloys. Such alloys tend to have a temperature induced phase change that will cause the material to have a preferred configuration that can be fixed by heating the material above a certain transition temperature to induce a change in the phase of the material. When the alloy is cooled back down, the alloy will "recall" the shape it was in during the heat treatment and will tend to assume that configuration unless constrained from doing so.

One particularly desirable memory shape alloy for use in the present disclosure is nitinol, an approximately stoichiometric alloy of nickel and titanium, which may also include minor amounts of other metals to achieve desired properties. Nickel-titanium alloys are very elastic and are commonly referred to as "superelastic" or "pseudoelastic." The elasticity of these alloys helps a medical device return to an expanded configuration for deployment inside of the body following passage in a distorted or collapsed form through a delivery catheter. Nitinol is a particularly desirable alloy for forming the collapsible medical devices of the present disclosure.

The metal wires used to fabricate the collapsible medical devices of the present disclosure may include wires having a diameter of from about 0.002 to about 0.008 inches (about 0.051 to about 0.203 millimeters), including from about 0.002 to about 0.005 inches (about 0.051 to about 0.127 millimeters). In some embodiments the wires have a diameter of from about 0.003 to about 0.0035 inches (about 0.076 to about 0.089 millimeters), and in some other embodiments, about 0.003 inches (about 0.076 millimeters). In one specific embodiment, the wires have a diameter of about 0.006 inches (about 0.152 millimeters). The number of wires in a wire mesh fabric (or tubular braid) may vary from about 36 to about 144, desirably from about 72 to about 144, and in some embodiments, 144. The pick count of the wire mesh may vary from about 30 to about 100, including from about 50 to about 80, including 70. As noted above, the wire diameter and the number of wires in the wire mesh fabric will tend to influence the rigidity, strength, and flexibility of the resulting collapsible medical device. Numerous other embodiments and combinations of wires sizes are contemplated within the scope of this disclosure.

In one specific embodiment of the present disclosure, a collapsible medical device including an open lumen from a proximal end to a distal end is formed from a braided tubular member by providing securement/attachment points (marker bands, for example as described below) on both the proximal end and the distal end of the braided tubular member. This embodiment is particularly useful when a collapsible medical device is desired that has attachment points on both ends of the device to allow for attachment to two separate additional medical devices. Additionally, this embodiment is particularly desirable when a collapsible medical device is desired that comprises only a single layer of material.

In this particular forming process, the braided tubular member as described above is first marked with braid markers (fabric ties, for example) into the number of sections that will ultimately be combined into the securement/attachment points; that is, the braided tubular member is sectioned-off as desired using braid markers to create the desired number of securement/attachment points in the end device. For example, if it is desired to form a collapsible medical device including an open lumen that has 12 securement/attachment points, then the braided tubular member would be sectioned with 12 braid markers. Although the braid markers may be introduced onto the tubular member in any suitable manner, the braid markers are generally tied around each individual section so as to form a tied bundle or tied section of wires. This tying of the braid markers around each bundle or section of wires allows each braid marker to be easily removed later in the forming process as described herein by simply untying each braid marker. In some embodiments of this forming method, the braided tubular member may be placed on a mandrel or in a former or mold prior to the introduction of the braid markers so as to hold the braid stationary during the coupling process and to assist in the introduction of the braid markers onto the braided tubular member. When more than one braid marker is used, the braid markers are generally spaced evenly around the circumference of the braided tubular member, though this is not required in all embodiments. In one exemplary embodiment, when it is desired to produce a collapsible medical device including four securement/attachment points on the collapsible medical device, four braid markers are first evenly positioned around the circumference of the braided tubular member in order to create four distinct sections for further manipulation to create the desired open lumen from the proximal end to the distal end of the braided tubular member.

Turning now to the Figures, FIG. 1 illustrates a braided tubular member including braid markers suitable for use in forming one embodiment of a collapsible medical device of the present disclosure. Braided tubular member 2 has a proximal end 4, and a distal end 6, includes braided wires 8, and braid markers 10, 11, 12, and 13. Braid markers 10, 11, 12, and 13 are generally evenly spaced about the circumference of braided tubular member 2 such that in subsequent processing steps as described herein, four generally equal sections of braided wires 8 are created. Distal wire ends 9 and proximal wire ends 15 are also shown in FIG. 1.

Figure 2:
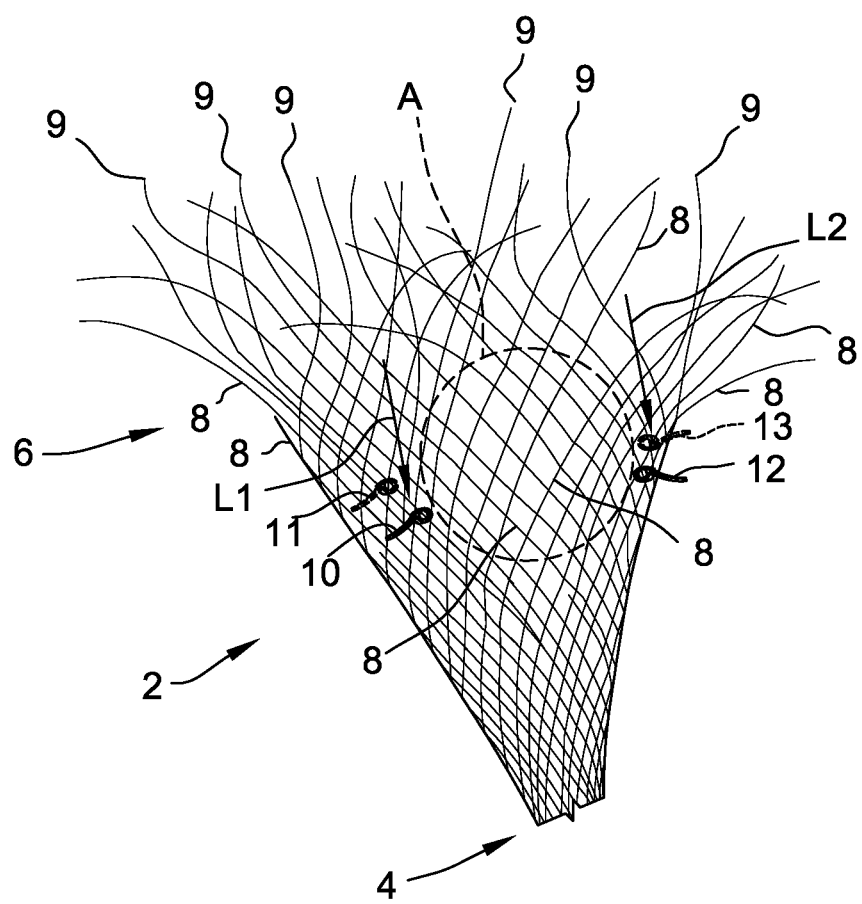
FIG. 2 is the braided tubular member of FIG. 1 illustrating unraveled portions thereof during formation of the collapsible medical device.

Once braid markers 10, 11, 12, and 13 have been introduced onto braided tubular member 2 as illustrated in FIG. 1 and described above, braided wires 8 are picked-out or unraveled from the distal wire ends 9 on distal end 6 of braided tubular member 2 toward braid markers 10, 11, 12, and 13 in a generally straight longitudinal line. Referring now to FIG. 2, there is shown braided tubular member 2 including braid markers 10, 11, 12, and 13 wherein braided wires 8 on distal end 6 have been unraveled along longitudinal lines L1 and L2 (toward proximal end 4) to create unraveled wire ends 9 such that the circled portion A remains in a substantially braided pattern. This unraveling in a generally straight line to each braid marker 10, 11, 12, and 13 from distal end 6 of braided tubular member 2 allows the braided pattern of braided wires 8 between braid markers 10, 11, 12, and 13 to be substantially maintained; that is, the braided pattern of braided wires 8 between braid markers 10, 11, 12 and 13 is not unraveled and remains substantially intact.

After the desired unraveling of braided wires 8 to braid markers 10, 11, 12, and 13 has been completed as described above, wire ends 9 between each of braid markers 10, 11, 12, and 13 are separated and collected into separate and distinct bundles. For example, when four braid markers have been utilized as described above, the wire ends on the braided tubular member will be collected into four separate bundles of wire ends. (If six braid markers are used, the wire ends would be collected in six separate and distinct bundles, etc.) In other words, the quantity of braid markers may match the quantity of bundles. Each of the bundles of wire ends then has a marker band (or other similar attachment/securement device) introduced thereon to hold and secure the wire ends in place and provide an attachment point.

Figure 3:
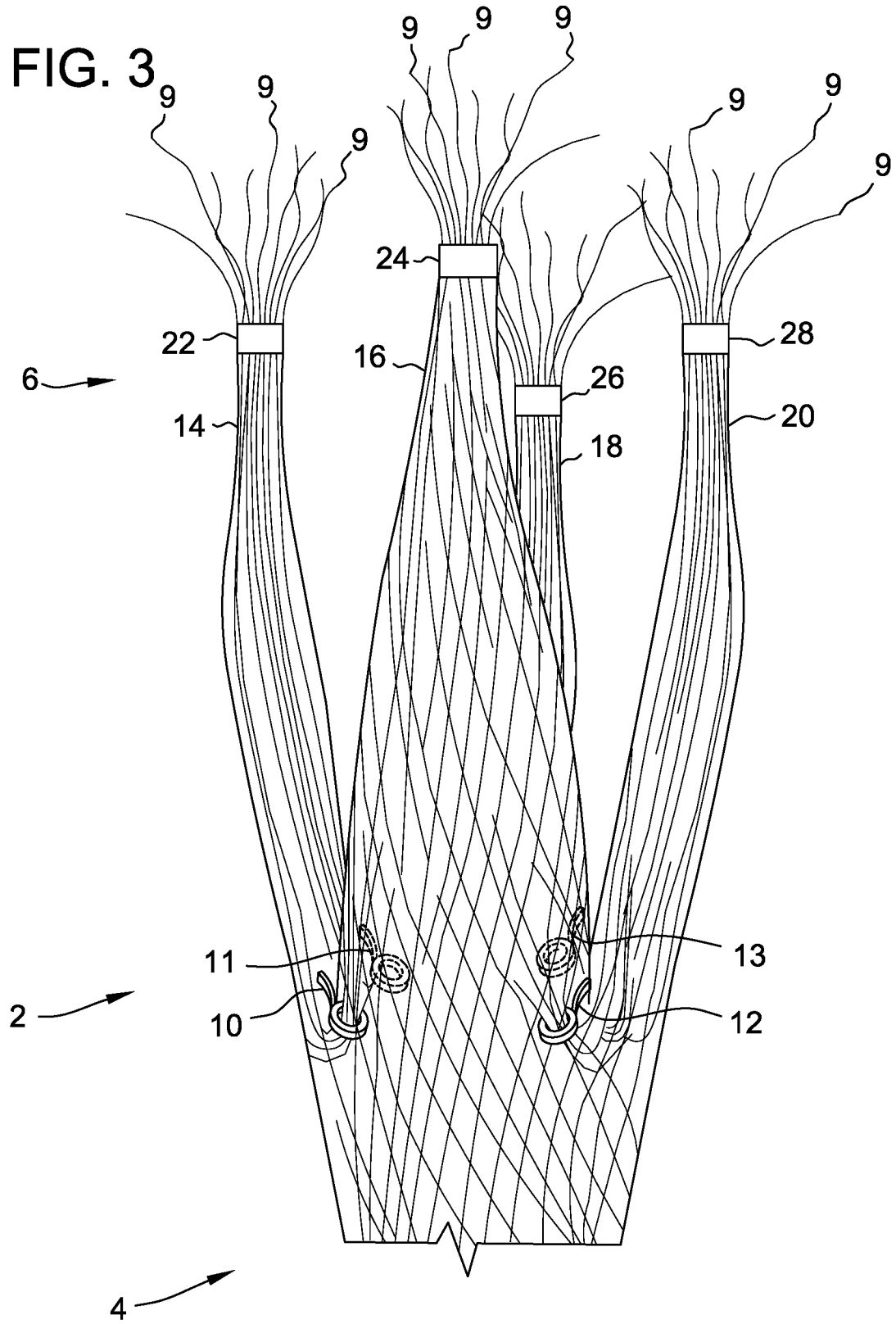
FIG. 3 is the braided tubular member of FIG. 2 illustrating the placement of various marker bands near the distal end of the braided tubular member.

Turning now to FIG. 3, there is shown braided tubular member 2 in a collapsed (or elongated) conformation having proximal end 4, distal end 6, braid markers 10, 11, 12, and 13, wire ends 9, and including wire bundles 14, 16, 18, and 20. Each of wire bundles 14, 16, 18, and 20 include a marker band 22, 24, 26, and 28, respectively. Before marker bands 22, 24, 26, and 28 are permanently attached to wire bundles 14, 16, 18, and 20 as described below (by welding, soldering, adhesive, or the like), braided tubular member 2 may be optionally collapsed (or elongated) so that all of the wire ends are substantially the same length. By collapsing braided tubular member 2 during manufacturing, the resulting medical device including the open lumen will collapse to a smaller profile upon its use. When the smallest possible profile is not required for the medical device having an open lumen (for example when the resulting medical device is to be coupled to another medical device that has a larger collapsed profile thus necessitating the need for a larger deliver device), elongation during manufacturing is not required, although it still may be useful in some embodiments. The collapsible medical devices of the present disclosure including an open lumen from a proximal end to a distal end thereof may be formed to include 1, 2, 3, 4, 5, 6, 7, 8, 9, 10, 11, 12, or more securement/attachment points as disclosed herein. The securement/attachment points may be located on both ends of the collapsible medical device (See FIGS. 4 and 5) or only on a single end of the collapsible medical device (See FIGS. 7 and 8), and allow the collapsible medical device to be attached to one or more other medical devices or delivery devices.

After marker bands 22, 24, 26, and 28 have been positioned on wire bundles 14, 16, 18, and 20 respectively, marker bands 22, 24, 26, and 28 are slid down wire bundles 14, 16, 18, and 20 placed at least a minimum distance away from their respective braid markers in order to allow the formation the complete through lumen. This proper placement at some distance from the respective braid markers allows the braid the ability to expand properly as the desired wire length between braid markers is maintained. In many embodiments, the desired minimum distance for placement may be affected by the braid diameter, the forming diameter, and the number of connections desired. Generally, it is desirable that the wires from the braid marker to the marker band closely follow their helical pattern and be long enough to accommodate the formed diameter, which allows it to fit over a desired mandrel for forming.

After marker bands 22, 24, 26, and 28 are placed in the desired position, they are welded (or otherwise attached by solder, adhesive, etc.) to wire bundles 14, 16, 18, and 20 and any excess wire strands are trimmed as desired using laser trimming or a suitable alternative process.

Once marker bands 22, 24, 26, and 28 have been attached to wire bundles 14, 16, 18, and 20 on distal end 6 of braided tubular member 2, a similar process as described above is utilized on proximal end 4 of braided tubular member 2 to form wire bundles including marker bands thereon and maintain the desired open lumen from proximal end 4 to distal end 6.

Figure 4:
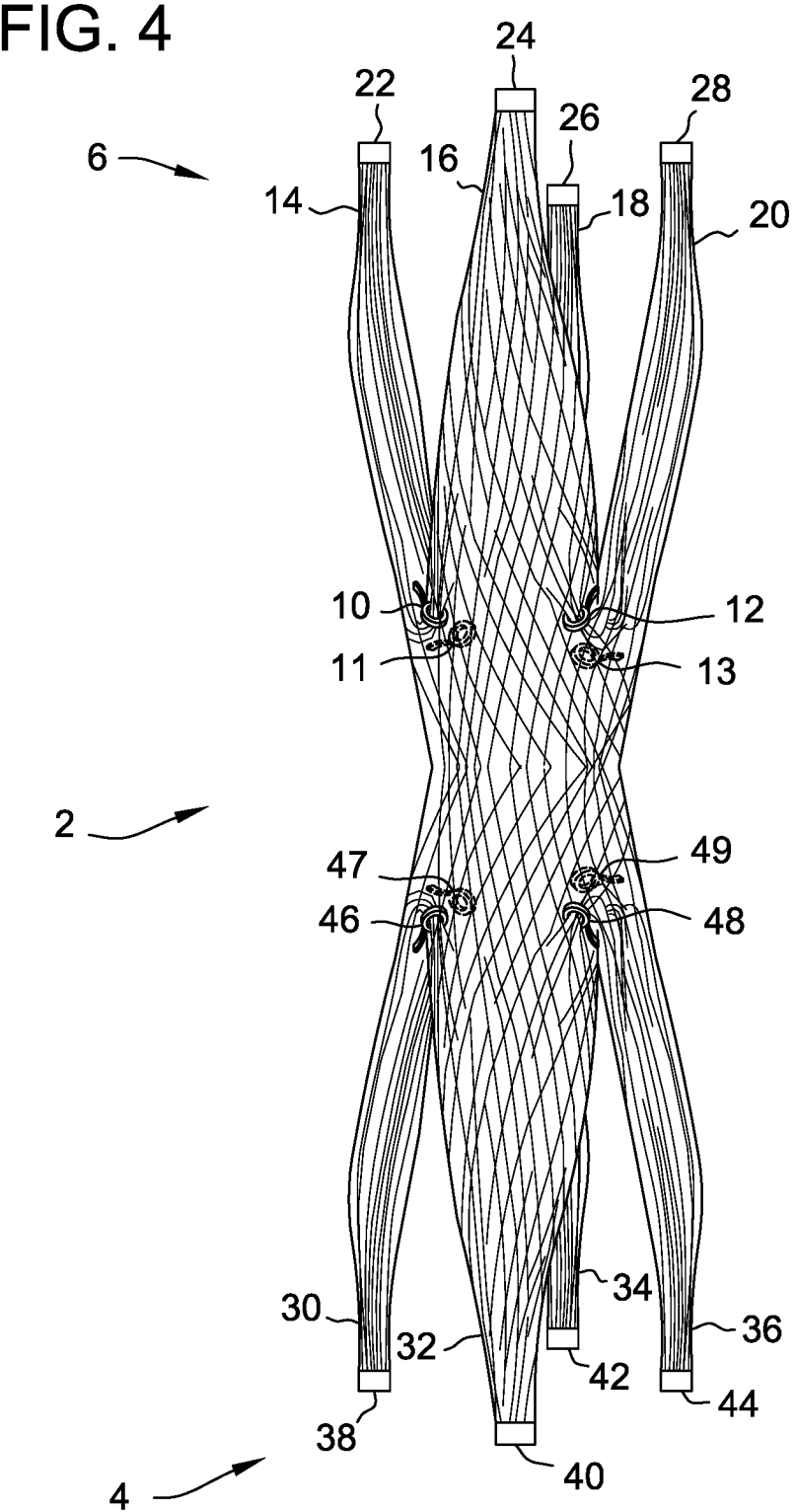
FIG. 4 is the braided tubular member of FIG. 3 further illustrating the proximal end of the braided tubular member.

Referring now to FIG. 4, there is shown braided tubular member 2 in collapsed (elongated) conformation having proximal end 4 and distal end 6. Distal end 6 includes wire bundles 14, 16, 18, and 20 having marker bands 22, 24, 26, and 28 thereon, respectively. Braid markers 10, 11, 12, and 13 are also shown. Proximal end 4 further includes wire bundles 30, 32, 34, and 36 having marker bands 38, 40, 42, and 44 thereon. Also shown on proximal end 4 are braid markers 46, 47, 48, and 49. An open lumen (not shown in FIG. 4) extends from proximal end 4 to distal end 6.

After marker bands 22, 24, 26, and 28 are secured to wire bundles 14, 16, 18, and 20 on distal end 6 of braided tubular member 2 and marker bands 38, 40, 42, and 44 are secured to wire bundles 30, 32, 34, and 36 on proximal end 4 of braided tubular member 2 as described above and the open lumen extending from proximal end 4 to distal end 6 maintained, all of the braid markers 10, 11, 12, 13, 46, 47, 48, and 49 may be removed from braided tubular member 2 by untying each of braid markers 10, 11, 12, 13, 46, 47, 48, and 49. Although is some embodiments it may be desirable to remove the braid markers, such removal is not required in all embodiments. Because the wire lengths are set, braided tubular member 2 may then be formed and heat treated into a suitable desired shape using heat-treating processes and methodologies known on the art for medical devices and memory-shape alloys.

Figure 5:
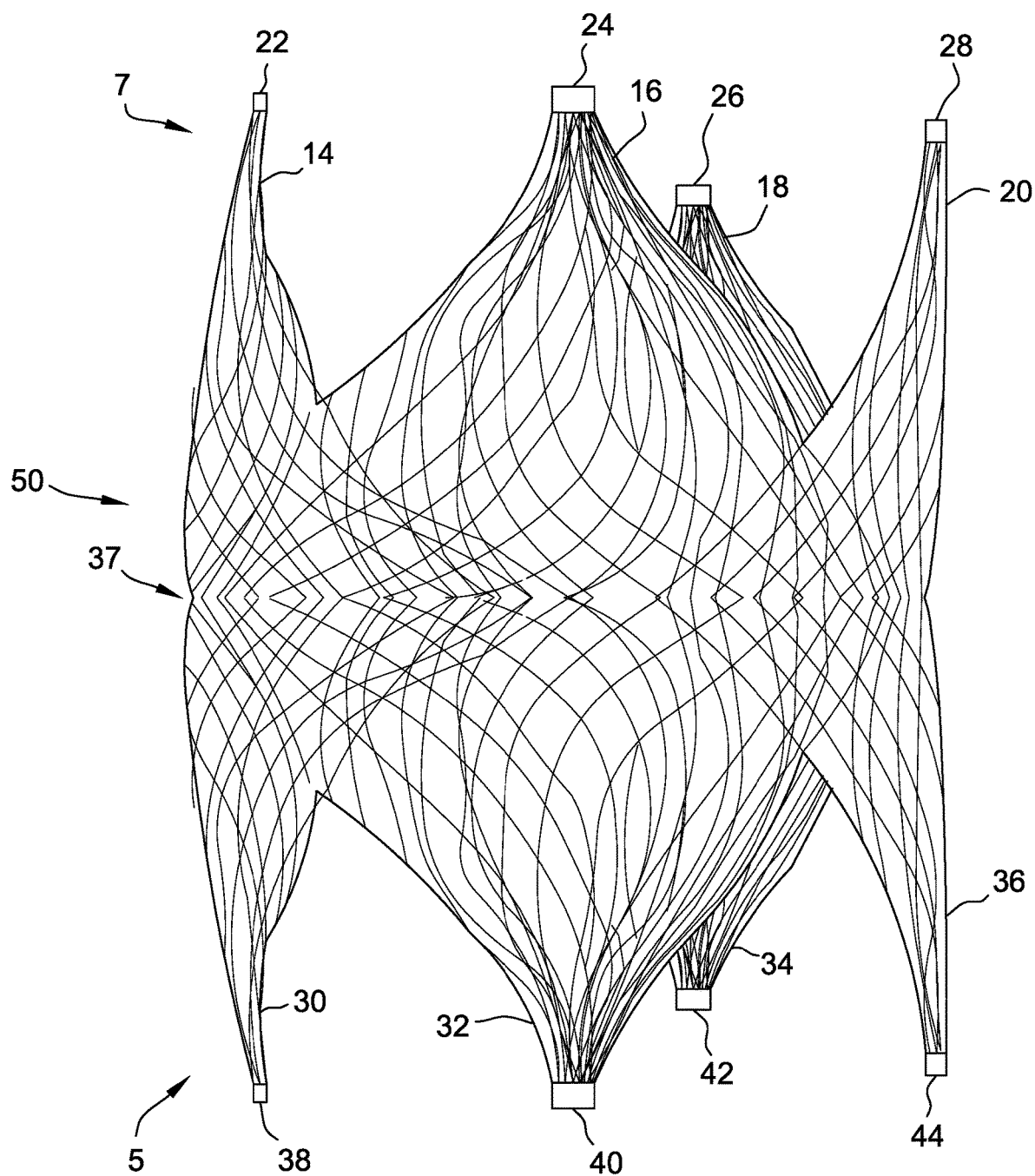
FIG. 5 is the braided tubular member of FIG. 4 after it has been heat-treated into a desired pre-set configuration.

Turning now to FIG. 5, there is illustrated braided tubular member 2 of FIG. 4 after it has been heat-treated into a desired pre-set configuration to form heat set collapsible medical device 50. Heat set collapsible medical device 50 includes center portion 37, proximal end 5 and distal end 7. Proximal end 5 and distal end 7 of heat set collapsible medical device 50 generally correspond respectively with proximal end 4 and distal end 6 of braided tubular member 2 of FIG. 4. Proximal end 5 of heat set collapsible medical device 50 includes marker bands 38, 40, 42, and 44 securing wire bundles 30, 32, 34, and 36, respectively. Distal end 7 of heat set collapsible medical device 50 includes marker bands 22, 24, 26, and 28 securing wire bundles 14, 16, 18, and 20, respectively. Heat set collapsible medical device 50 includes an open lumen extending from proximal end 5 to distal end 7.

Figure 6B:
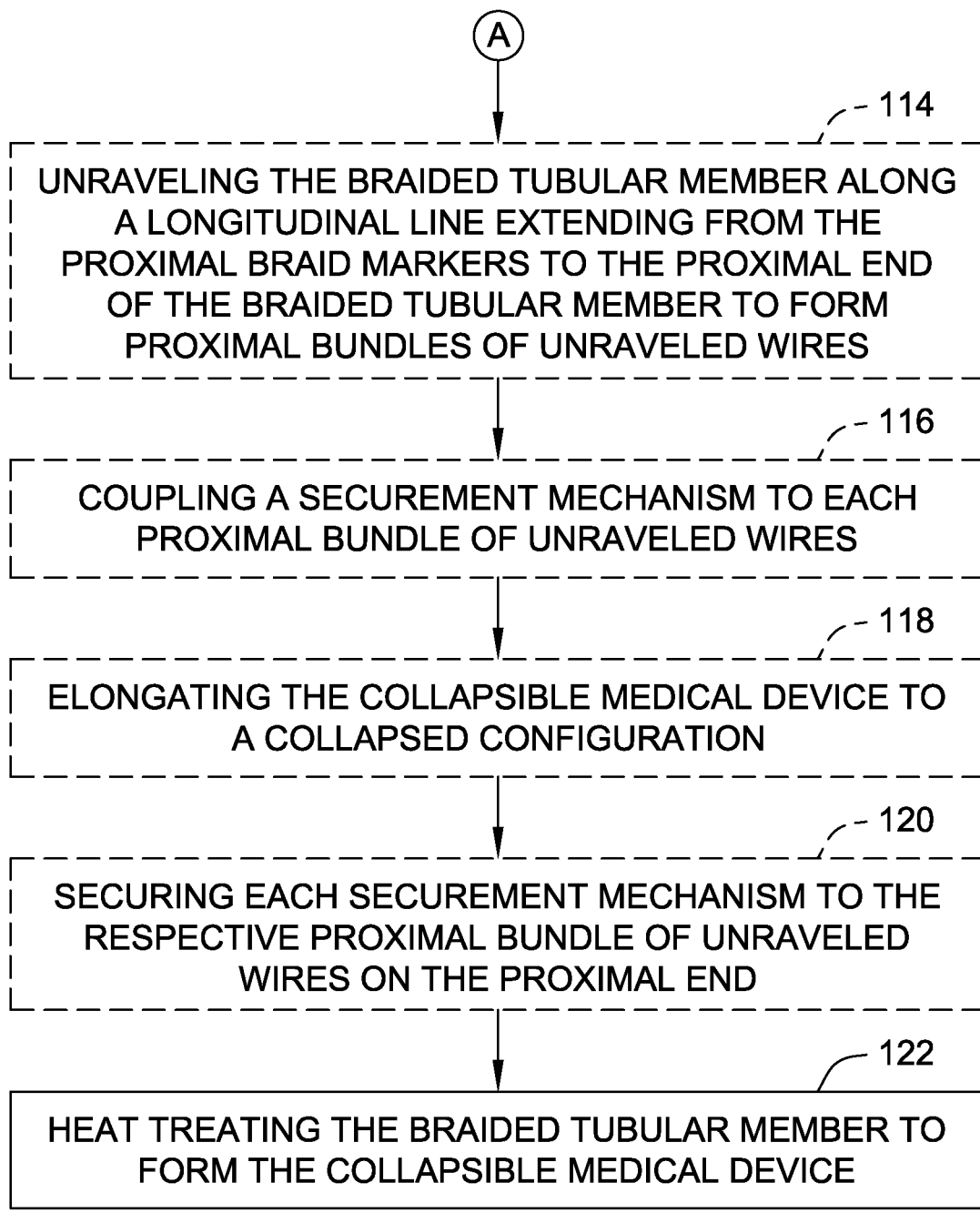

FIGS. 6A and 6B are flow diagrams of a method 100 for forming a collapsible medical device (such as medical device 50 shown in FIG. 5) having an open lumen from a proximal end to a distal end, according to one embodiment. Method 100 includes coupling 102 distal braid markers (such as braid markers 10, 11, 12, and 13), near a distal end of a braided tubular member (such as braided tubular member 2) comprising a plurality of braided wires (such as braided wires 8), and unraveling 104 the braided tubular member along a longitudinal line extending from the distal braid markers to the distal end of the braided tubular member to form distal bundles of unraveled wires (such as wire bundle 14, 16, 18, and 20). Method 100 further includes coupling 106 a securement mechanism (such as marker bands 22, 24, 26, and 28) to each bundle of unraveled wires. Method 100 further includes optionally elongating 108 the collapsible medical device to a collapsed configuration and securing 110 each securement mechanism to the respective bundle of unraveled wires. Method 100 further includes optionally coupling 112 proximal braid markers to a proximal end of the braided tubular member and unraveling 114 the braided tubular member along a longitudinal line extending from the proximal braid markers to the proximal end of the braided tubular member to form proximal bundles of unraveled wires. Method 100 further includes coupling 116 a securement mechanism to each proximal bundle of unraveled wires. Method 100 further includes elongating 118 the collapsible medical device to a collapsed configuration and securing 120 each securement mechanism to the respective proximal bundle of unraveled wires on the proximal end. Finally, method 100 includes heat treating 122 the braided tubular member to form the collapsible medical device.

In an alternative forming process of the present disclosure, a collapsible medical device having an open lumen from a proximal end to a distal end in accordance with the disclosure herein may be formed using a braided tubular member as described above having a proximal wire end and a distal wire end. In this alternative process, however, the proximal wire end is first inverted over itself toward the distal wire end. The inversion of the proximal end results in the formation of an inner layer and an outer layer (two separate layers) of the braided tubular member. The open lumen is maintained from the proximal end to the distal end of the inverted structure after the inversion. Additionally, with this alternative process, securement/attachment points are present on only one end of the resulting collapsible device. Collapsible medical devices formed using this alternative process may require a reduced number of steps in the collection and termination of the braid sections, thus making manufacturing easier and more cost effective.

Additionally, the inversion of the proximal end over itself as described herein creates a clean, well-defined end that is desirable for deploying a graft or other medical device that requires precise placement accuracy without having the braid attachment sections extend beyond the length of the device. Moreover, the inverted end may have higher radial force as compared to the rest of the device due to the geometry of the inverted wires, which may be desirable in some embodiments where migration resistance is desirable. Further, the two layers created by the inversion of the proximal end can readily accept and house a third, potentially more occlusive layer, therebetween to improve the resulting properties of the finished device. In some embodiments, a third metallic layer, such as a braided nitinol layer of the like, for example, may be introduced between the inner and outer layer formed by the inversion of the proximal end. In other embodiments, a third fabric layer, such as a braided polyester fabric layer or the like, for example, may be introduced between the inner and outer layer formed by the inversion of the proximal end. In some embodiments, the two layers created by the inversion can house two, three, four or more additional layers therein.

After the inversion of the proximal end and the forming of the inner and outer layers, the proximal wire end and the distal wire end are aligned generally or substantially longitudinally for further manufacturing. Once the longitudinal alignment of the proximal wire end the distal wire end is complete, the process proceeds generally as disclosed above to form the final device. In particular, one or more braid markers are attached (depending upon how many securement/attachment points are desired, as described above) to both the inner layer and the outer layer to allow further processing of both layers. In some embodiments, the inverted braided tubular member may be placed on a mandrel, or in a former or mold, prior to the introduction of the braid markers so as to hold the braid stationary during the coupling process. Additionally, in some embodiments as noted above, the inner layer and the outer layer may house therebetween one or more additional layers, such as another metallic layer (nitinol or the like) to increase the occlusive properties of the resulting medical device. When present, this third, in-between metallic layer, will have been introduced between the two layers formed by the inversion and subsequently longitudinally aligned with these two layers and will also have braid markers attached thereto such that all three layers are brought together and coupled by the braid markers and prepared for further manufacturing as described herein. After the braid markers are attached to both the inner layer and the outer layer (and optionally the third in-between metallic layer as noted above), both layers are simultaneously unraveled along a generally longitudinal line that extends from each braid marker to the proximal end wire and the distal end wire (which are longitudinally aligned as noted above) to form one or more sections of unraveled wires between each braid marker (or one set of unraveled wires if a single braid marker is utilized).

Once the unraveling is complete and the formed sections gathered, a securement/attachment mechanism, such as a marker band, is coupled to each section of unraveled wires. After the securement mechanism(s) has been coupled to the unraveled wire section(s), the braided tubular member may be optionally elongated as described above, and each securement mechanism is secured to each section of unraveled wires after proper positioning. In this embodiment, because the proximal end of the starting braided tubular member is inverted over itself and longitudinally aligned with the distal end after inversion, only one set of securement/attachment mechanisms is needed to form the collapsible medical device; that is, in this forming process only one end of the structure will include securement/attachment mechanisms. As with the previous embodiments described above, once the securement mechanisms have been secured to the sections of unraveled wires, the resulting structure may be heat treated into a desired heat set configuration, which includes an open lumen from a proximal end to a distal end.

In some embodiments of the present disclosure, it may be desirable to provide a medical device that has substantial occlusive properties; that is, occlusive properties that may be generally challenging to obtain using solely braided metallic layers. To form such a device having increased occlusive properties in accordance with the present disclosure, a third (or more) occlusive fabric layer, such as a braided polyester fabric layer, may be introduced between the inner and outer layers formed by the inversion as described above. In this embodiment when a braided fabric layer is desirable, braid markers are first placed on both the inner and outer layers (the two layers formed by the inversion) as described above, and these two layers unraveled together toward the braid markers as set forth herein. Separate marker bands are then placed on the inner layer and the outer layers such that the marker bands line up generally on top of each other but the layers continue to be separated. After this, the inner and outer layers are heat treated to set the desired final shape (this is done prior to the introduction of the braided fabric layer due to the melting point of the fabric being lower than the heat set temperatures). After heat treatment to set the shape is complete, the braided fabric layer (or the like) is placed in between the inner layer and the outer layer and marker bands are placed on the inner and outer layer together to form the device including three separate layers. The braided fabric layer (or the like) may then be sutured or otherwise attached in one or more locations to the inner and outer layer to restrict its movement and hold it in the desired location. The marker bands initially placed on the inner and outer layers are then removed such that the remaining marker bands secure the layers and provide a device with increased occlusive properties. In some embodiments, it may be desirable for the braided fabric layer to be positioned within the inner and outer layers such that is it at or near the end of rolled over end to increase the occlusive properties of the resulting device.

Figure 7:
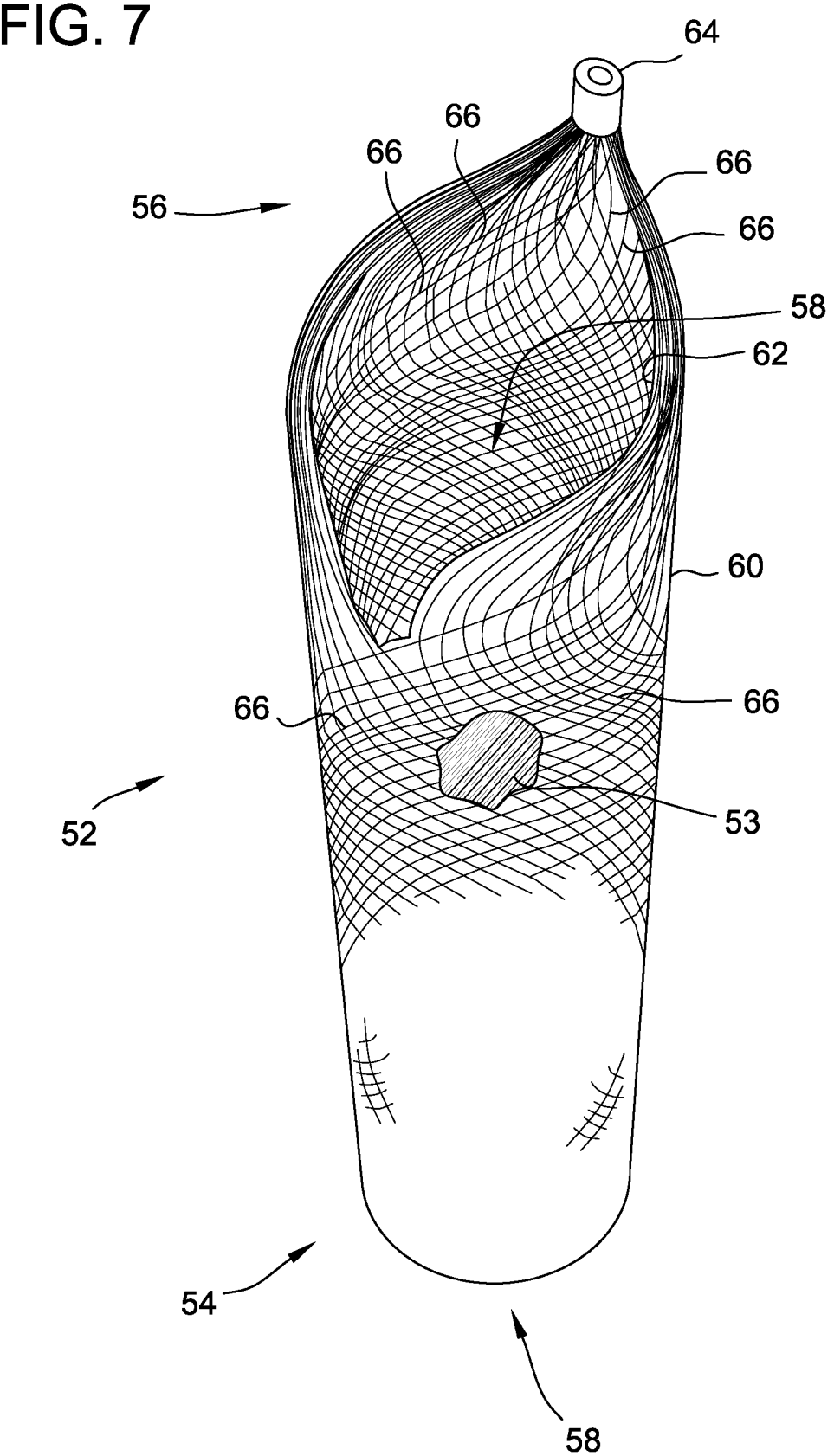
FIG. 7 is a perspective view of a collapsible medical device including an open lumen in accordance with one embodiment of the present disclosure.

Turning now to FIG. 7, there is illustrated a collapsible medical device including an open lumen from a distal end to a proximal end formed in accordance with the alternative forming embodiment described above including the initial inversion of a braided tubular member over itself to form a dual layer structure. FIG. 7 shows collapsible medical device 52 including proximal end 54 and distal end 56. An open lumen 58 extends between proximal end 54 and distal end 56 to allow fluids to pass therethrough without obstruction. Collapsible medical device 52 also includes outer layer 60, inner layer 62, and middle fabric layer 53 located between outer layer 60 and inner layer 62 (as shown in FIG.

7 with outer layer 60 partially cut away to reveal middle fabric layer 53). As illustrated in FIG. 7, collapsible medical device 52 includes a single marker band 64 on distal end 56 securing wires 66 in place while maintaining open lumen 58.

Figure 8:
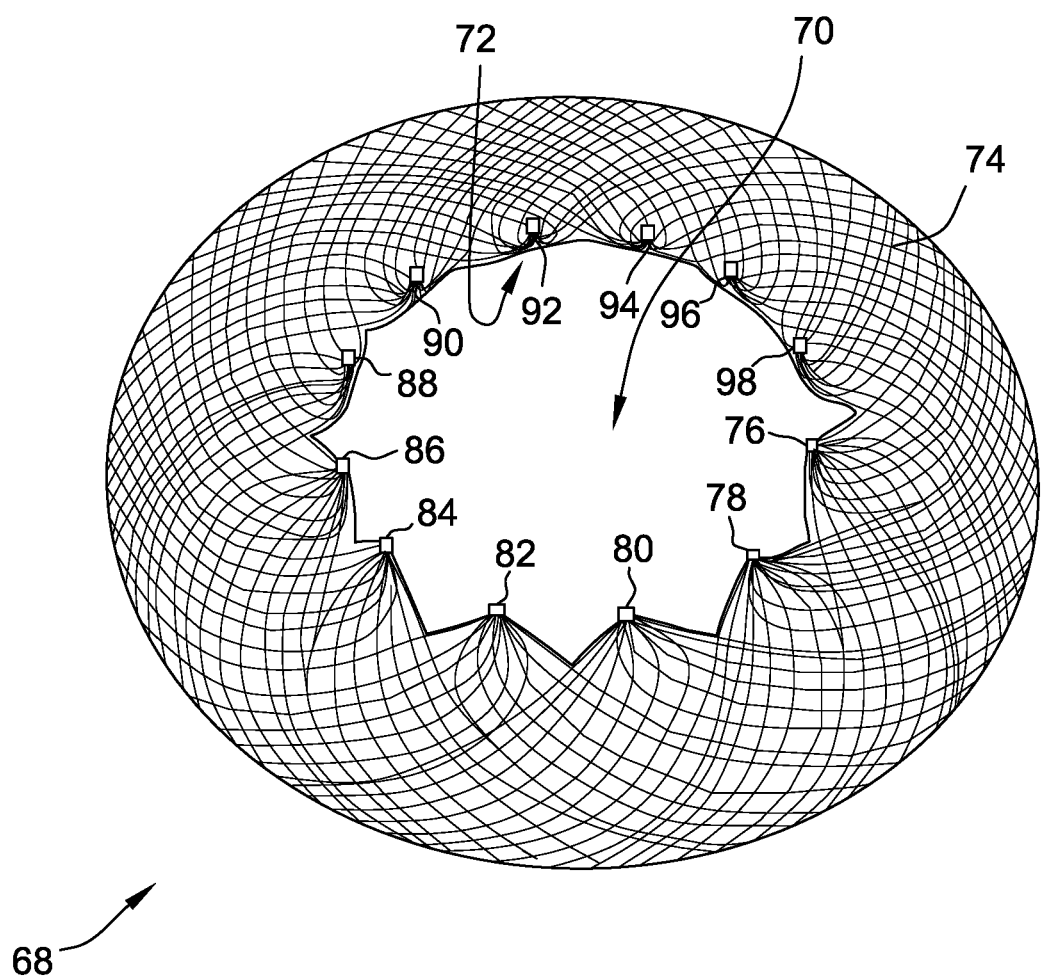
FIG. 8 is a perspective view of a collapsible medical device including an open lumen in accordance with another embodiment of the present disclosure.

Referring now to FIG. 8, there is shown another collapsible medical device including an open lumen from a distal end to a proximal end formed in accordance with the alternative embodiment described above including the inversion of a braided tubular member over itself to form a dual layer structure. FIG. 8 shows collapsible medical device 68 including open lumen 70. Collapsible medical device 68 further includes inner layer 72 and outer layer 74. As illustrated in FIG. 8, collapsible medical device 68 includes marker bands 76, 78, 80, 82, 84, 86, 88, 90, 92, 94, 96, and 98. Thus, collapsible medical device 68 provides 12 points of attachment.

Figure 9A:
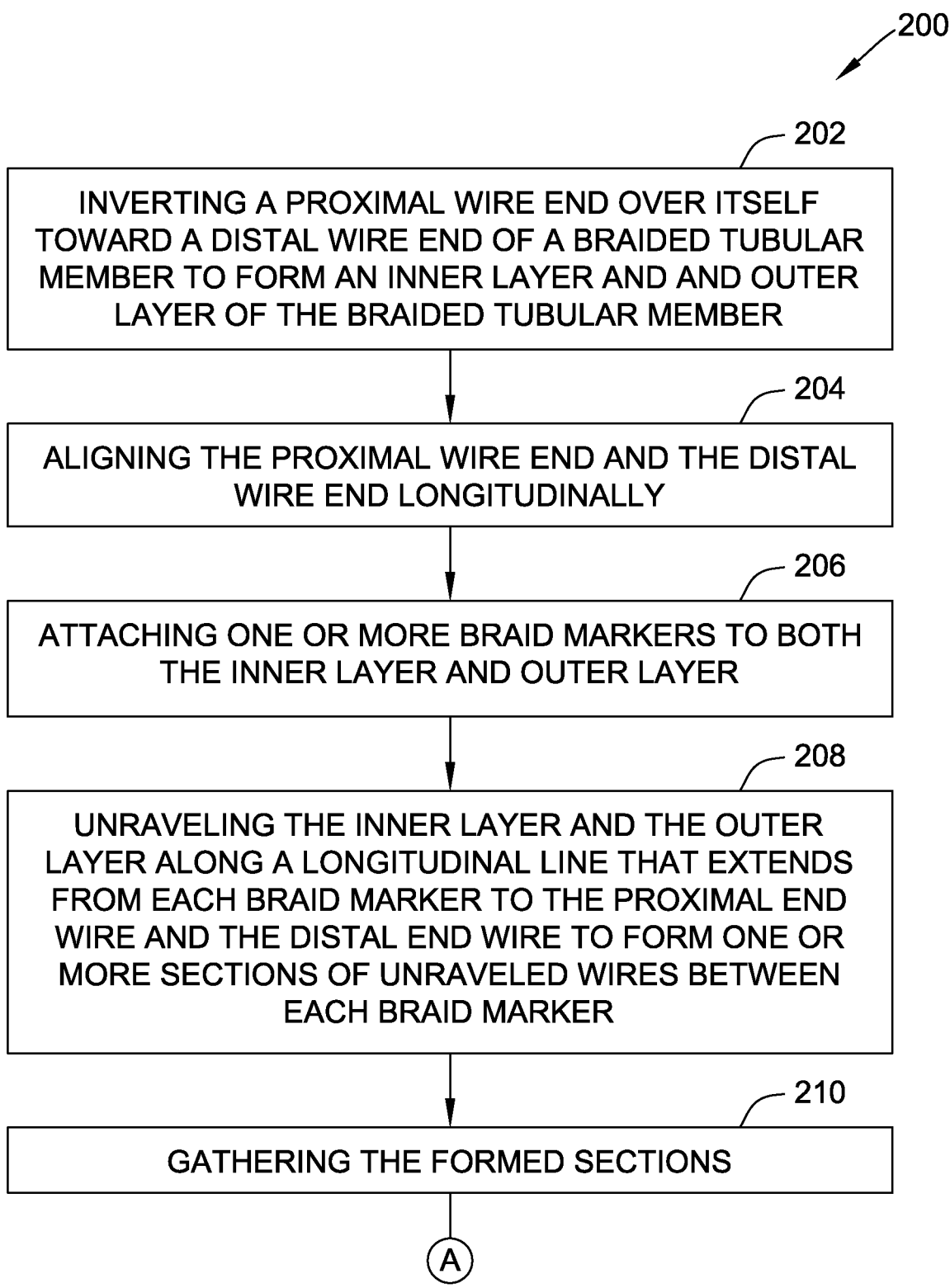
FIGS. 9A and 9B are flow diagrams of a method of forming a collapsible medical device including an open lumen.
Figure 9B:
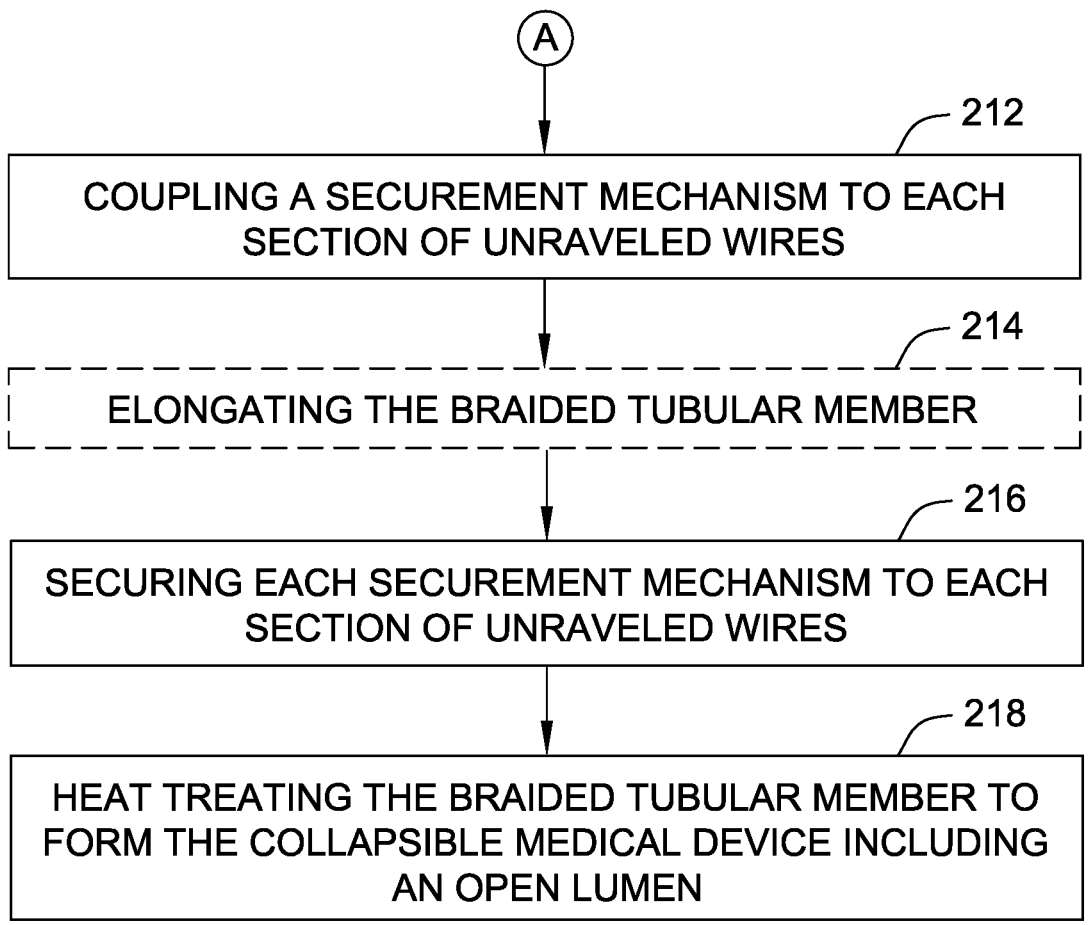

FIG. 9 is a flow diagram of a method 200 for forming a collapsible medical device (shown in FIG. 8) having an open lumen extending from a proximal end to a distal end. Method 200 includes inverting 202 a proximal wire end over itself toward a distal wire end of a braided tubular member to form an inner layer and an outer layer (two separate layers, but connected or continuously formed from a single braided tubular member) of the braided tubular member. Method 200 further includes aligning 204 the proximal wire end and the distal wire end longitudinally and attaching 206 one or more braid markers (depending upon how many securement points are desired, as described above) to both the inner layer and the outer layer. Method 200 further includes unraveling 208 the inner layer and the outer layer along a longitudinal line that extends from each braid marker to the proximal end wire and the distal end wire to form one or more sections of unraveled wires between each braid marker (or one set of unraveled wires if a single braid marker is utilized), gathering 210 the formed sections, and coupling 212 a securement mechanism to each section of unraveled wires. Method 200 further includes elongating 214 the braided tubular member and securing 216 each securement mechanism to each section of unraveled wires. Finally, method 200 includes heat treating 218 the braided tubular member to form the collapsible medical device including an open lumen.

The collapsible medical devices of the present disclosure including an open lumen extending from a distal end to a proximal end may be used as standalone medical devices or may be used in combination with another medical device or multiple other medical devices. When used as a standalone medical device, the attachment point or points present on the device may be attached directly to a delivery device. When used in combination with another medical device, the attachment points present on the device may be attached directly to the other medical device. By having an open lumen from a proximal end to a distal end as described herein, the collapsible medical devices of the present disclosure allow fluids and/or materials to pass therethough without significant obstruction.

Figure 10:
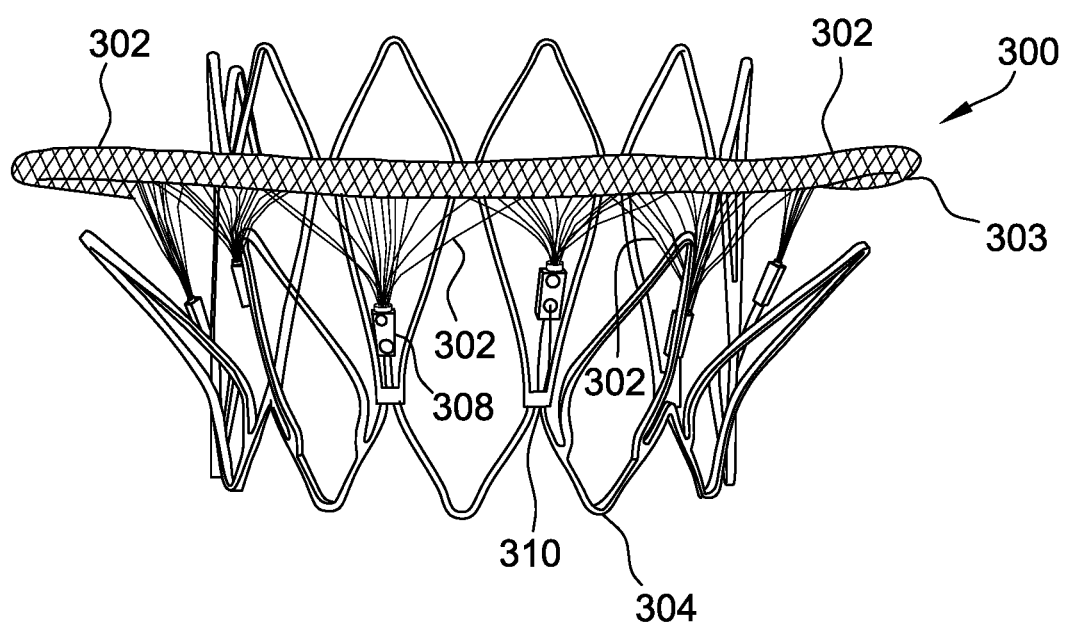
FIG. 10 is a side view of a collapsible medical device of the present disclosure used in combination with a mitral valve.
Figure 11:
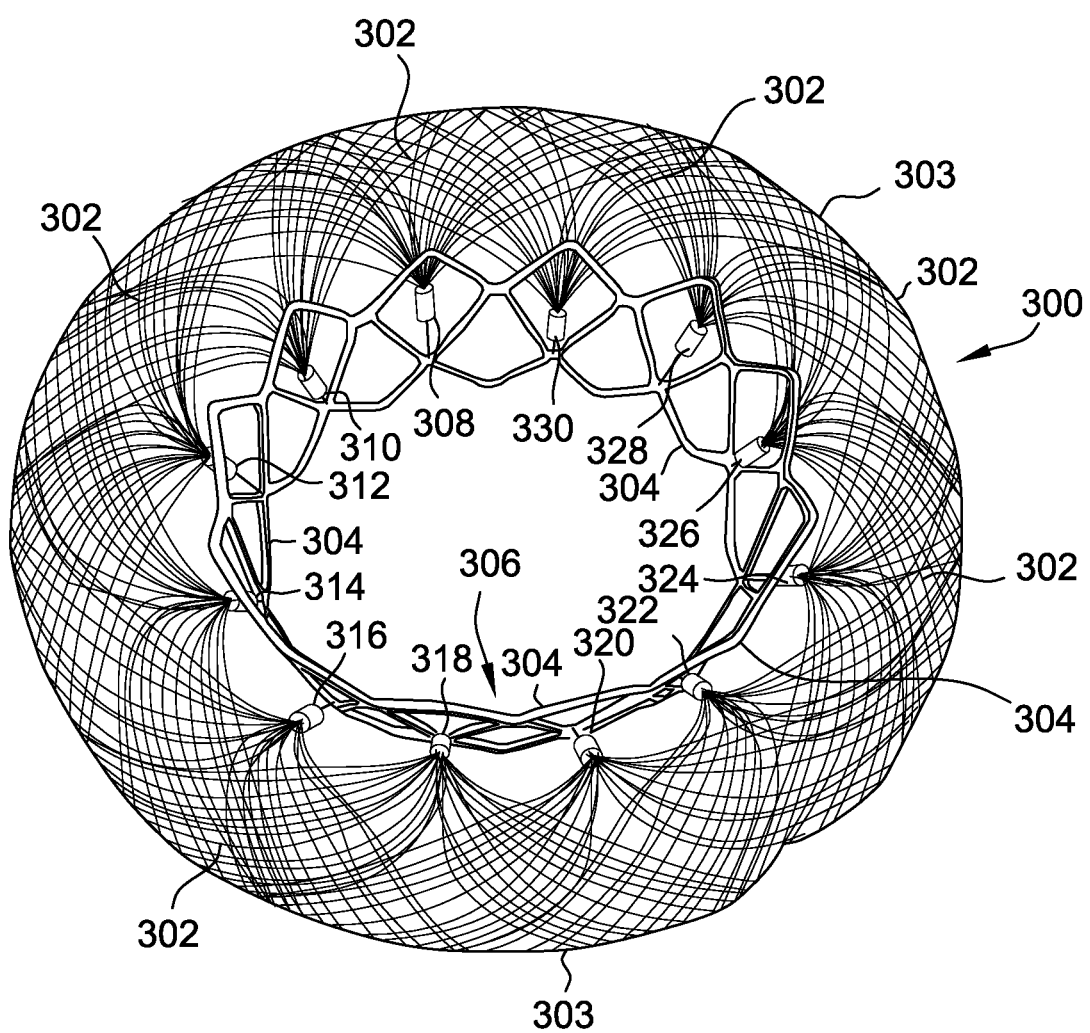
FIG. 11 is a top view of the collapsible medical device of the present disclosure and mitral valve of FIG. 10.

Referring now to FIGS. 10 (side view) and 11 (top view), there is shown a collapsible medical device of the present disclosure formed to include 12 securement points used in combination with a secondary medical device (a mitral valve) that includes 12 attachment points for mating with the 12 securement points on the collapsible medical device to allow the devices to be securely coupled to one another for use. Such coupling as described herein allows both devices to assume the same conformation (collapsed or expanded) as desired during introduction and use in the body. As illustrated in FIGS. 10 and 11, collapsible medical device 300 includes wires 302 forming braided tubular member 303, which is attached to mitral valve 304. Mitral valve 304 extends through collapsible medical device 300 through open lumen 306 such that mitral valve 304 may be introduced into the body at the desired location without interference from collapsible medical device 300.

Collapsible medical device 300 is coupled to mitral valve 304 at attachment points 308, 310, 312, 314, 316, 318, 320, 322, 324, 326, 328, and 330. Although illustrated in FIGS. 10 and 11 as a crimp weld, collapsible medical device 300 may be attached to mitral valve 304 in many different ways including, for example, by adhesive, by welding, by soldering, by suture, by fabric, and the like. Further, although illustrated in FIGS. 10 and 11 as including 12 attachment points and 12 securement points, collapsible medical device 300 and mitral valve 304, respectively, may include any number attachment and securement points that enables collapsible medical device 300 and mitral valve 304 to be coupled to one another.

In the embodiment illustrated in FIGS. 10 and 11, collapsible medical device 300 is sized and configured to seal against the left atrium when used in combination with mitral valve 304, although other configurations and uses are within the scope of the present disclosure. This configuration allows fluid to easily pass through mitral valve 304 during use while still allowing collapsible medical device 300 to perform its intended sealing function.

Although a number embodiments of this disclosure have been described above with a certain degree of particularity, those skilled in the art could make numerous alterations to the disclosed embodiments without departing from the spirit or scope of the disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A collapsible medical device comprising:
   a tubular member formed of a plurality of wires and having a preset, expanded configuration and a collapsed configuration, the tubular member having a center portion wherein the wires are in a braided configuration, and a distal end and a proximal end wherein the wires are in an unraveled configuration;

an open lumen extending from the proximal end to the distal end configured to allow passage of a fluid therethrough in the preset, expanded configuration;

at least one braid marker coupled to the tubular member at an interface between the center portion and the proximal end;

at least one braid marker coupled to the tubular member at an interface between the center portion and the distal end;

at least one securement mechanism coupled to the proximal end;

at least one securement mechanism coupled to the distal end;

wherein each securement mechanism is configured to secure at least a portion of the plurality of wires in the unraveled configuration near an outer circumference of the open lumen; and wherein the plurality of wires in the unraveled configuration are unraveled along a longitudinal line between the respective at least one securement mechanism coupled to the proximal and distal ends and the respective at least one braid marker at the interfaces between the center portion and the proximal and distal ends.

2. The collapsible medical device of claim 1, wherein the at least one securement mechanism coupled to the proximal and distal ends is a marker band.

3. The collapsible medical device of claim 1, wherein the plurality of wires are constructed of a memory-shape alloy.

4. The collapsible medical device of claim 3, wherein the memory-shape alloy is nitinol.

5. The collapsible medical device of claim 1, wherein the plurality of wires are substantially the same length.

6. The collapsible medical device of claim 1, wherein the device includes from 1 to about 12 securement mechanisms on each of the proximal end and the distal end.

* * * * *